(12) United States Patent
Murthy et al.

(10) Patent No.: US 7,338,640 B2
(45) Date of Patent: Mar. 4, 2008

(54) THERMOPILE-BASED GAS SENSOR

(75) Inventors: Sunil Srinivasa Murthy, Chennai (IN); Anis Zribi, Rexford, NY (US); Shankar Chandrasekaran, Chennai (IN)

(73) Assignee: General Electric Company, Schenectady, NY (US)

( * ) Notice: Subject to any disclaimer, the term of this patent is extended or adjusted under 35 U.S.C. 154(b) by 207 days.

(21) Appl. No.: 11/095,243

(22) Filed: Mar. 31, 2005

(65) Prior Publication Data
US 2006/0220164 A1 Oct. 5, 2006

(51) Int. Cl.
*B32B 5/02* (2006.01)
*B32B 27/04* (2006.01)
*B32B 27/12* (2006.01)
*G01N 7/00* (2006.01)
*G01N 21/00* (2006.01)

(52) U.S. Cl. .......................... 422/83; 422/50; 422/88; 422/95; 374/10; 374/11; 374/12; 374/13; 374/29; 374/31; 374/100; 436/43; 436/147; 436/149; 436/155

(58) Field of Classification Search .............. 422/50, 422/83, 88, 95; 374/10, 11, 12, 13, 29, 31, 374/100; 436/43, 147, 149, 155
See application file for complete search history.

(56) References Cited

U.S. PATENT DOCUMENTS

| | | | |
|---|---|---|---|
| 5,059,543 A | 10/1991 | Wise et al. | 437/3 |
| 5,343,064 A | 8/1994 | Spangler et al. | 257/350 |
| 5,596,219 A * | 1/1997 | Hierold | 257/467 |
| 5,863,803 A | 1/1999 | Zanini-Fisher et al. | 436/147 |
| 5,982,014 A | 11/1999 | Paige | 257/467 |
| 5,988,875 A * | 11/1999 | Gershfeld et al. | 374/10 |
| 6,106,149 A * | 8/2000 | Smith | 374/31 |
| 6,190,035 B1 * | 2/2001 | Smith | 374/31 |
| 6,339,187 B1 * | 1/2002 | Inoue | 136/225 |

FOREIGN PATENT DOCUMENTS

EP  1039280 A2  9/2000

OTHER PUBLICATIONS

Smith et al., "Determining the Effects of Vapor Sorption in Polymers with the Quartz Crystal Microbalance/Heat Conduction Calorimeter," Journal of Polymer Science: Part B: Polymer Physics, vol. 42, pp. 3893-3906, Wiley Periodicals, Inc. (2004).*

* cited by examiner

*Primary Examiner*—Brian Sines
(74) *Attorney, Agent, or Firm*—Fletcher Yoder

(57) ABSTRACT

A method of manufacturing a sensor is provided. The method includes disposing a sacrificial layer on a substrate, disposing a low-thermal-conductivity layer on the sacrificial layer, and disposing a first set of conductive arms and a second set of conductive arms on the low-thermal-conductivity layer to form a plurality of thermal junctions. The plurality of thermal junctions is adapted to form a plurality of hot junctions and a plurality of cold junctions when subjected to a difference in temperature. The method also includes removing the sacrificial layer and a portion of the low-thermal-conductivity layer to form a cavity therein. The cavity is configured to provide insulation for the plurality of hot junctions. A thermopile sensor is also provided, and a calorimetric gas sensor implementing the thermopile sensor is provided.

14 Claims, 4 Drawing Sheets

THERMOPILE-BASED GAS SENSOR

BACKGROUND

The invention relates generally to the field of miniaturized sensors and, more specifically, to highly sensitive thermopile-based gas sensors.

A thermopile sensor is a set of thermocouples connected in series for obtaining a larger signal output. Thermocouples measure the temperature difference between the hot and cold junctions by generating an electromotive force (emf) caused by a phenomenon known as the Seebeck effect, as appreciated by those of ordinary skill in the art. Thus, a thermopile adds up the emf of all the thermocouples to provide a higher voltage output. Thermal isolation in thermopiles is achieved by providing a thin diaphragm region and a relatively large heat sink.

Silicon is used as a substrate material for thermopiles. However, there is typically a high amount of heat loss in such thermopiles because silicon is thermally conductive. Attempts have been made to prevent such heat losses because heat loss tends to result in decreased thermopile efficiency. Thermal isolation between the hot and the cold junctions may be provided by etching a section of the silicon substrate under the hot junction while providing thermal insulation through a multiple stacked structure. However, even after etching the silicon substrate, conductive heat losses occur through the thermal insulating layers.

Attempts have been made to stack numerous thermopiles together to increase thermopile output resolution. Such devices involve creating separate thermopiles and then bonding them together. However, such attempts have proven to be costly, time-consuming and difficult to implement because of the need for separate etching for each thermopile that is bonded together.

An improved thermopile sensor that has higher sensitivity and reduced cost is therefore desirable.

SUMMARY

A method of manufacturing a sensor is provided. The method includes disposing a sacrificial layer on a substrate, disposing a low-thermal-conductivity layer on the sacrificial layer, disposing a first set of conductive arms and a second set of conductive arms on the low-thermal-conductivity layer to form a plurality of thermal junctions. The plurality of thermal junctions is adapted to form a plurality of hot junctions and a plurality of cold junctions when subjected to a difference in temperature. The method also includes removing the sacrificial layer and a portion of the low-thermal-conductivity layer to form a cavity therein. The cavity is configured to provide insulation for the plurality of hot junctions. A thermopile sensor is also provided, and a calorimetric gas sensor implementing the thermopile sensor is provided.

These and other advantages and features will be more readily understood from the following detailed description of preferred embodiments of the invention that is provided in connection with the accompanying drawings.

DETAILED DESCRIPTION OF EXEMPLARY EMBODIMENTS

Figure 1:
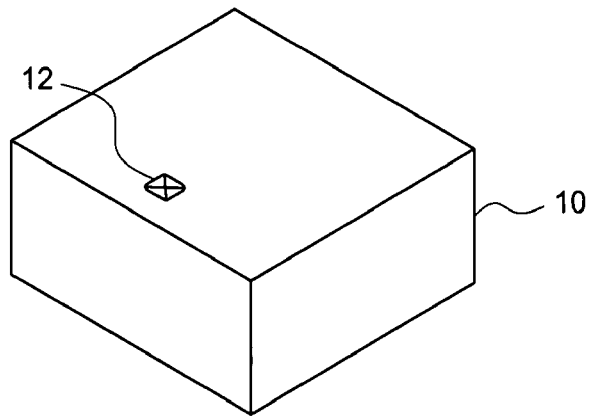
FIG. 1 is a diagrammatical view of a system including an exemplary thermopile sensor in accordance with an embodiment of the invention.

FIG. 1 is a diagrammatical view of a system 10 including an exemplary thermopile sensor 12 in accordance with one aspect of the present technique. The system 10 may be a closed or an open vessel in which temperature is measured. In one embodiment, the thermopile sensor 12 may be coupled with the system 10 to measure the temperature of the gas within the system 10. However, in various other embodiments, one or more thermopile sensors 12 may be utilized.

Figure 2:
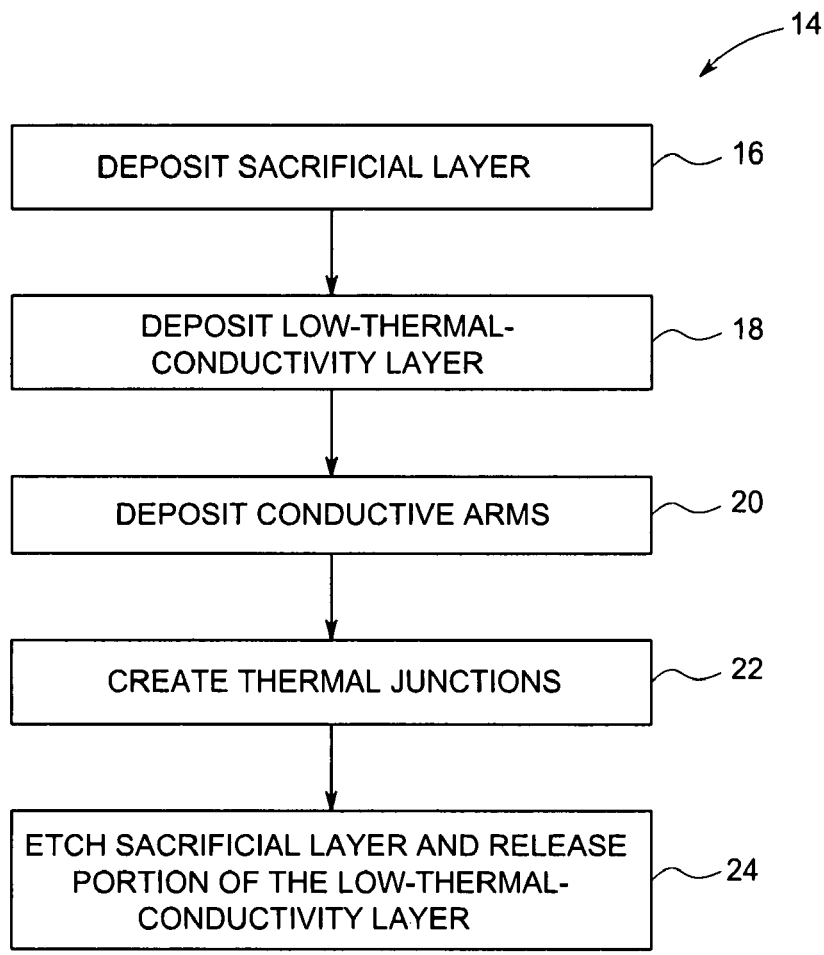
FIG. 2 is a flow chart illustrating a fabrication process of an exemplary thermopile sensor in accordance with one aspect of the present technique.

Referring generally to FIG. 2, a flow chart illustrating a fabrication process 14 of a thermopile sensor 12 in accordance with certain embodiments of the present technique is shown. In the illustrated embodiment, the fabrication process 14 begins at Step 16 by deposition of a sacrificial layer over a substrate wafer. The sacrificial layer may serve as a supporting layer on which other conductive or insulation layers may be built. The sacrificial layer may then be etched out to form a cavity.

A low-thermal-conductivity layer is deposited over the sacrificial layer at Step 18. The low-thermal-conductivity layer may serve as a thermal insulation layer for preventing heat leakages. A set of conductive arms, such as metal strips or conductive semiconductor strips, may be deposited at Step 20 to form the arms of individual thermocouples that together form the thermopile sensor. The ends of the conductive arms may be electrically coupled to form thermal junctions at Step 22. These thermal junctions form the "hot" and "cold" junctions of the thermopile. The sacrificial layer may then be etched out along with a portion of the low-thermal-conductivity layer to form a cavity at Step 24. This air-filled cavity enhances the thermal insulation so that heat leakages from the hot junction to the cold junction or from the hot junction through the base substrate are minimized. The details of the fabrication process 14 will become better understood in the description that follows.

Figure 3:
FIGS. 3-7 are cross-sectional views of a thermopile sensor at various points in a fabrication process in accordance with an embodiment of the invention.

Referring generally to FIGS. 3 through 9, cross-sectional views of an exemplary micro-fabricated thermopile sensor at various points in a fabrication process, in accordance with aspects of the present technique are shown. In FIG. 3, a sacrificial layer 28 is deposited on a semiconductor wafer 26 (Step 16, FIG. 2). The semiconductor wafer 26, which may comprise a p-type silicon wafer having resistivity of about 50 ohm-cm, forms a substrate for deposition of other layers. The sacrificial layer 28 may include a phospho-silicate-glass material having a thickness of about 0.2 micrometer.

Figure 4:

As shown in FIG. 4, a low-thermal-conductivity layer 30 may be deposited on the sacrificial layer 28 (Step 18, FIG. 2). The low-thermal-conductivity layer 30 may include a nitride layer, such as a layer of silicon nitride ($Si_xN_y$) for example $Si_3N_4$, and may be deposited with a thickness of about 0.3 micrometer. The nitride layer 30 forms an insulation layer that reduces heat leakage, as will be described in detail below.

Figure 5:

As shown in FIG. 5, a polysilicon layer 32 may be deposited on the low-thermal-conductivity layer 30 for constructing a plurality of conductive arms. The polysilicon layer 32 may be made of a semiconductor material such as silicon ($Si_x$).

Figure 6:
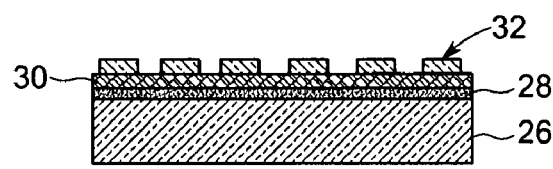

Turning now to FIG. 6, there is shown etching of the polysilicon layer 32 to form electrode lines. The polysilicon layer 32 may be patterned and etched to form a plurality of electrode lines or two sets of strips.

Figure 7:
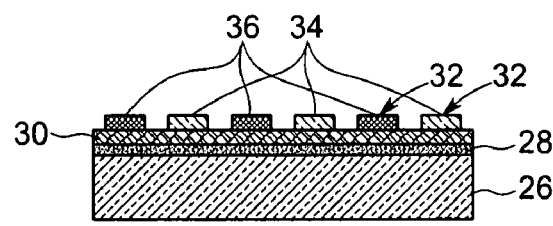

FIG. 7 shows masking and doping of one set of electrode lines shown in FIG. 6. In particular, a first set of strips 34 are masked by deposition of a masking layer. A second set of strips 36 is then doped to form $p^+$ doped silicon conductive arms 36 via an ion implantation process.

Figure 8:
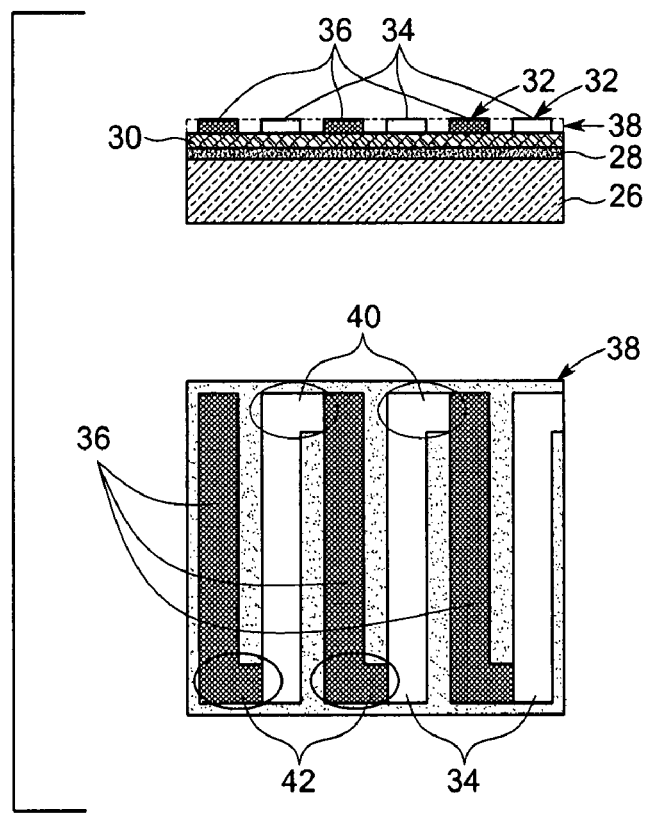
FIG. 8 illustrates a cross-sectional view and a top-view of a first layer of the thermopile sensor of FIG. 7.

FIG. 8 illustrates a cross-sectional view and a top-view of a first layer of the thermopile sensor, highlighting the masking and doping of another set of electrode lines shown in FIG. 6. As shown, the second set of strips 36 are masked by deposition of a masking layer and the first set of strips 34 are doped to form $n^-$ doped silicon conductive arms 34. As will be appreciated by one of ordinary skill in the art, the operations described with reference to FIGS. 7 and 8 may be performed in either order. For example, the operations shown in FIG. 7 may follow the operations shown in FIG. 8. In such a case, the second set of strips 36 may be masked initially to dope the first set of strips 34 and form $n^-$ doped silicon conductive arms 34. Then, the first set of strips 34 may be masked for doping the second set of strips 36 to form $p^+$ doped silicon conductive arms 36. Similarly, $n^-$ doped silicon conductive arms 34 and $p^+$ doped silicon conductive arms 36 may be formed in either of the operations shown in FIG. 7 or 8. When these sets of conductive arms 34 and 36 are formed, these conductive arms 34 and 36 may be electrically coupled to form a plurality of thermal junctions 38 (Step 22, FIG. 2). The thermal junctions may include "hot" junctions 40 and "cold" junctions 42.

Figure 9:
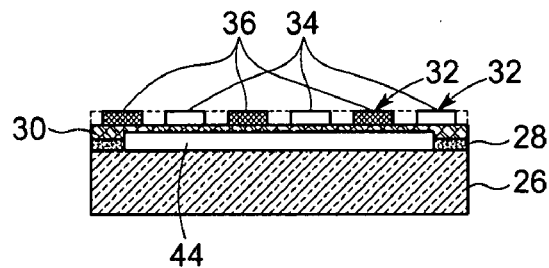
FIG. 9 is a cross-sectional view of the thermopile sensor of FIG. 8.

Turning now to FIG. 9, the sacrificial layer 28 and a portion of the low-thermal-conductivity layer 30 may be removed by etching to form a cavity 44. The cavity 44 provides insulation between the hot junctions 40 and the cold junctions 42. Also, the cavity 44 helps to reduce heat-sinking from the hot junctions 40 to the substrate layer 28. The operations discussed above with respect to FIGS. 3-9 illustrate cross-sectional views at various points during the fabrication process of a single layer of $n^-/p^+$ junction pair thermopile sensor. Thermal insulation of the hot junction 40 is achieved through the release of the sacrificial layer 28 and a portion of the low-thermal-conductivity layer 30 to form the air-gap or cavity 44.

In another embodiment, the operations referred to with respect to FIGS. 3 and 4 may be performed prior to the deposition of a first set of metallic conductive arms and a second set of metallic conductive arms. The first and the second set of metallic conductive arms may be made of different metals, for example aluminum, bismuth, antimony, copper, and the like or alloys such as Constantan. The specific combination of metals or metal-alloy combination is matters of design choice. For example, the set of metallic conductive arms may be chosen such that one set possesses a positive Seebeck coefficient, while the other set possesses a negative Seebeck coefficient. By releasing the sacrificial layer 28 and a portion of the low-thermal-conductivity layer 30, the air-gap or cavity 44 may then be formed, as illustrated in FIG. 9.

In still another embodiment, the operations described with respect to FIGS. 3-6 may be performed to form the first set of strips. Then the first set of strips may be doped to form either $n^-$ doped silicon conductive arms 34 or $p^+$ doped silicon conductive arms 36. These operations may be performed as illustrated in FIG. 7 or FIG. 8, respectively. If $n^-$ doped silicon conductive arms 34 are formed, then a set of metallic conductive arms with a positive Seebeck coefficient may be deposited to form the second set of conductive arms. Alternatively, if $p^+$ doped silicon conductive arms 36 are formed, then a set of metallic conductive arms with a negative Seebeck coefficient may be deposited to form the second set of conductive arms. By releasing the sacrificial layer 28 and a portion of the low-thermal-conductivity layer 30, as shown in FIG. 9, the air-gap or cavity 44 may then be formed.

Figure 10:
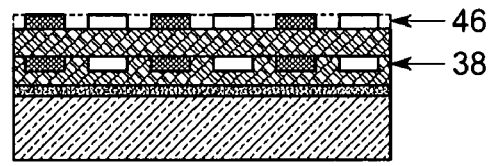
FIG. 10 is a cross-sectional view of the thermopile sensor of FIG. 8.
Figure 11:
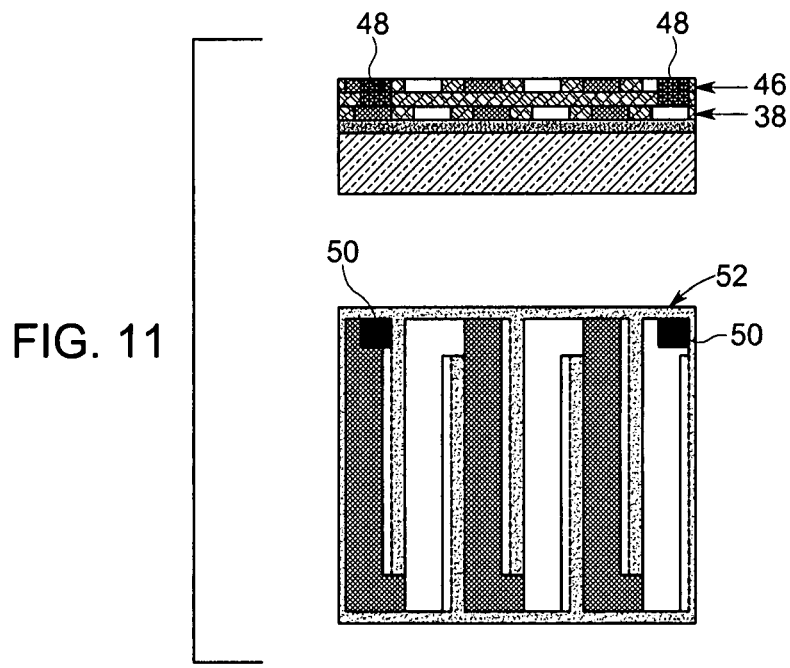
FIG. 11 illustrates a cross-sectional view and a top-view of the thermopile sensor of FIG. 10.

Referring now to FIGS. 10 and 11, an embodiment of a multi-layered thermopile structure having various layers of $n^-/p^+$ junction pair thermopile sensors is shown. FIG. 10 illustrates a multi-layered thermopile structure. During the fabrication of the multi-layered thermopile structure, operations described with respect to FIGS. 3-8 may be performed to form $n^-$ doped silicon conductive arms 34 and $p^+$ doped silicon conductive arms 36. These operations form the first layer 38 of $n^-/p^+$ junction pair thermopile sensor. However, as described previously, the conductive arms in the first layer 38 of the thermopile sensor may be a combination of metallic conductive arms and doped semiconductor arms, such as $p^+$ doped silicon arms or $n^-$ doped silicon arms. Alternatively, the first layer 38 of the thermopile sensor may include only metallic conductive arms. These conductive arms may then be electrically coupled to form thermal junctions, for example hot and cold junctions. When the first layer 38 of the thermopile sensor is fabricated, a second layer 46 of thermopile sensor may be fabricated over the first layer 38, by following the operations described with reference to FIGS. 4-8. Similarly, a plurality of thermopile layers may be fabricated by repeating the operations described with reference to FIGS. 4-8. Again, the plurality of layers may comprise a combination of $p^+$ doped silicon arms and $n^-$ doped silicon arms, or a combination of metallic conductive arms and doped semiconductor conductive arms, or only sets of metallic conductive arms, as had been described previously in the various embodiments. Although only two thermopile layers 38 and 46 have been shown, additional layers may be fabricated.

FIG. 11 shows electrical coupling of various layers of the multi-layered thermopile structure. When a desirable number of layers are achieved, the multilayered structure shown in FIG. 10, may be defined with a photoresist for etching holes 48. The holes 48 thus formed may be deposited with metallic contacts 50 to electrically couple the thermopile sensor layers 38 and 46. It may be noted that each of the thermopile layers may be fabricated slightly offset with respect to the previous layer for ease of achieving electrical coupling, such as Schottky metal contacts. For example, the second layer 46 may be fabricated slightly offset with respect to the first layer 38, as shown in block 50, which is a top view of the multilayered structure showing metallic contacts 50 that couple the conductive arms of the two thermopile sensor layers 38 and 46.

Applications for embodiments of the invention may be found in differentially measuring or tracking the temperature of a location with respect to a reference location maintained at a reference temperature. Similarly, other parameters such as concentration or presence of a gas within an enclosure may be detected. For example, a highly sensitive thermopile sensor constructed in accordance with the present technique may be utilized in a calorimetric gas sensor for detecting the presence of a gas or the concentration of the gas.

Figure 12:
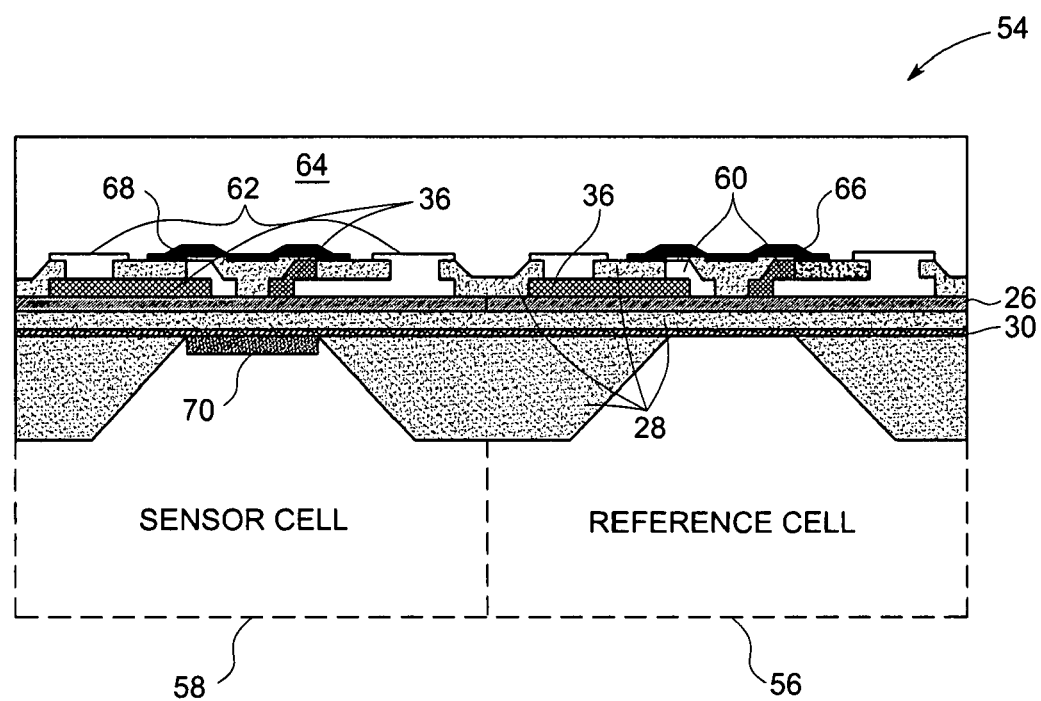
FIG. 12 is a cross-sectional view of an exemplary calorimetric gas sensor including a thermopile sensor, in accordance with one aspect of the present technique.

FIG. 12 shows a cross-sectional view of an exemplary calorimetric gas sensor 54 including a thermopile sensor, in accordance with aspects of the present technique. The calorimetric gas sensor 54 may comprise a reference cell 56 and a sensor cell 58. The calorimetric gas sensor 54 may be fed with the gas whose concentration is to be determined. A thermopile sensor may be coupled to the micro-fabricated calorimetric gas sensor 54 so that hot junctions 60 and cold junctions 62 of the thermopile sensor are thermally coupled to the reference cell 56 and the sensor cell 58. The thermopile sensor may be micro-fabricated with the calorimetric gas sensor 54 and may be enclosed in a closed enclosure 64 having an inert gas, for example Nitrogen ($N_2$), Argon (Ar), Helium (He), and the like. A reference cell heater 66 and a sensor cell heater 68 may be coupled with the reference cell 56 and sensor cell 58. The sensor cell 58 comprises an adsorbent material 70. This adsorbent layer 70 is adapted to absorb a defined amount of gas. Furthermore, the adsorbent layer 70 is adapted to desorb a portion of the adsorbed gas when heated.

The temperature of the reference cell 56 and the sensor cell 58 may be scanned within a temperature domain of interest. For example, the temperature scanning may be performed between room temperature of about 25 degrees Celsius to about 500 degrees Celsius. The temperature profile may be chosen such that total gas desorption occurs within the scanned interval. Because of the difference in heat capacities of the two cells 56 and 58 and because of the endothermal desorption of the gas from the adsorbent layer 70, the sensor cell 58 thermally lags behind the reference cell 56. For measuring the heat of desorption of the gas, this thermal lag may be compensated by heating the sensor cell 58 by providing more power into the sensor cell heater 68. The amount of power fed into the sensor cell heater 68 for achieving thermal equilibrium between the two cells 56 and 58 may be calibrated to read the concentration of the gas within the sensor cell 58. This is because the adsorbent layer 70 absorbs an amount of gas proportional to the concentration of the gas within the sensor cell 58. When the cells 56 and 58 are heated by the respective heaters 66 and 68, gas from the adsorbent layer 70 desorbs, thereby cooling the sensor cell 58. The temperature of the sensor cell 58 would thus fall proportional to the amount of gas absorbed by the adsorbent layer 70. Therefore, a proportional amount of power may be required to heat the sensor cell 58 to compensate for the thermal lag from the reference cell 56.

It will be appreciated by those of ordinary skill in the art that a closed loop for measuring the differential temperatures between the two cells 56 and 58 and utilizing that signal to adjust the power flow to the sensor cell 58 for matching its temperature to that of the reference cell 56, may be implemented. High sensitivity thermopiles, in accordance with aspects of the present techniques, may be fabricated such that the cold junctions 62 are located on the silicon frame (maintained at room temperature). In such a case, the hot junctions 60 may be located on the two cells 56 and 58 and would serve to directly measure the heat flux between the two cells 56 and 58. A voltage signal that is proportional to the differential temperature between the cells 56 and 58, may then be generated. This voltage signal may be used to adjust the power flow to the sensor cell 58. The differential power consumed in the two cells 56 and 58 correspond directly to the heat of desorption.

Moreover, the calorimetric gas sensor 54 may be operated in adsorption mode. For example, the heat generated in the sensor cell 58 because of adsorption of the gas by the adsorbent layer 70 may be measured. The amount of heat generated in the sensor cell 58 may be calibrated to read the concentration of the gas within the sensor cell 58.

The fabrication of thermopile sensor, as described hereinabove, produces an air-gap or air-cavity as illustrated, which can be distinguished by other fabrication methods known in the art, which remove the substrate to yield a free-standing membrane. Similarly, the calorimetric gas sensor 54 described hereinabove includes a thermopile sensor having a cavity fabricated by the abovementioned operations, as compared to other calorimetric gas sensors, such as catalytic calorimetric gas sensor, catalytic differential calorimetric gas sensor or calorimetric gas sensors utilizing resistance temperature detectors.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A calorimetric gas sensor, comprising:
   a reference cell;
   a sensor cell comprising an adsorbent layer configured to adsorb a defined amount of gas and to desorb a portion of the defined amount of gas when heated, wherein the sensor cell and the reference cell are fabricated on a sensor substrate;
   a thermopile sensor disposed on the sensor cell and the reference cell and configured to measure heat flux between the sensor cell and the reference cell, wherein the thermopile sensor comprises:
      a sacrificial layer disposed on a substrate;
      a low-thermal-conductivity layer disposed on the sacrificial layer;
      a first set of conductive arms and a second set of conductive arms disposed on the low-thermal-conductivity layer to form a plurality of thermal junctions, wherein the plurality of thermal junctions is adapted to form a plurality of hot junctions and a plurality of cold junctions when subjected to a difference in temperature, and wherein the sacrificial layer and the low-thermal-conductivity layer include a cavity etched therebetween.

2. The calorimetric gas sensor as recited in claim 1, comprising a heating mechanism configured to heat the sensor cell and the reference cell.

3. The calorimetric gas sensor as recited in claim 2, wherein the heating mechanism is configured to heat the sensor cell and the reference cell to a reference temperature.

4. The calorimetric gas sensor as recited in claim 3, wherein the sensor cell is configured to attain a final temperature when the portion of the defined amount of gas desorbs from the adsorbent layer, wherein the reference temperature is different from the final temperature.

5. The calorimetric gas sensor as recited in claim 4, wherein the calorimetric gas sensor produces a signal indicative of a concentration of the gas in the sensor cell based on a difference between the final temperature and the reference temperature.

6. A sensor, comprising:
a substrate;
a sacrificial layer disposed on the substrate;
a low-thermal-conductivity layer disposed on the sacrificial layer; and
a first set of conductive arms and a second set of conductive arms disposed on the low-thermal-conductivity layer to form a plurality of thermal junctions, wherein the plurality of thermal junctions is adapted to form a plurality of hot junctions and a plurality of cold junctions when subjected to a difference in temperature, and wherein the sacrificial layer and the low-thermal-conductivity layer include a cavity etched therebetween.

7. The sensor as recited in claim 6, wherein the substrate comprises a semiconductor substrate.

8. The sensor as recited in claim 6, wherein the sacrificial layer comprises a phospho-silicate glass layer.

9. The sensor as recited in claim 6, wherein the low-thermal-conductivity layer comprises a silicon nitride layer.

10. The sensor as recited in claim 6, wherein the cavity is configured to form a thermal insulation layer between the plurality of hot junctions and the plurality of cold junctions.

11. The sensor as recited in claim 6, wherein the first set of conductive arms comprises a set of p-doped conductive arms.

12. The sensor as recited in claim 6, wherein the second set of conductive arms comprises a set of n-doped conductive arms.

13. The sensor as recited in claim 6, wherein the first set of conductive arms comprises a set of metallic conductive arms.

14. The sensor as recited in claim 6, wherein the second set of conductive arms comprises a set of metallic conductive arms.

* * * * *